US007234824B2

(12) United States Patent
Langley

(10) Patent No.: US 7,234,824 B2
(45) Date of Patent: Jun. 26, 2007

(54) GLARE-ELIMINATION DEVICE FOR SURGICAL MICROSCOPES

(76) Inventor: Nicholas M. Langley, 265 Windsor Gate Cove, Atlanta, GA (US) 30342-2863

(*) Notice: Subject to any disclaimer, the term of this patent is extended or adjusted under 35 U.S.C. 154(b) by 55 days.

(21) Appl. No.: 10/946,408

(22) Filed: Sep. 21, 2004

(65) Prior Publication Data

US 2005/0063058 A1 Mar. 24, 2005

Related U.S. Application Data

(60) Provisional application No. 60/504,718, filed on Sep. 22, 2003.

(51) Int. Cl.
*A61B 19/08* (2006.01)
(52) U.S. Cl. .......................... 359/510; 359/507; 359/368
(58) Field of Classification Search ................ 359/507, 359/510, 511, 368; 600/121, 125
See application file for complete search history.

(56) References Cited

U.S. PATENT DOCUMENTS

| 2,285,658 | A | * | 6/1942 | Hitchcock ................... 359/513 |
|---|---|---|---|---|
| 3,796,477 | A | * | 3/1974 | Geraci ........................ 359/511 |
| 4,266,663 | A | * | 5/1981 | Geraci ........................ 359/510 |
| 4,385,812 | A | * | 5/1983 | Wille et al. ................. 359/511 |
| 5,311,358 | A | * | 5/1994 | Pederson et al. ........... 359/510 |
| 5,467,223 | A | * | 11/1995 | Cleveland et al. .......... 359/510 |
| 5,608,574 | A | * | 3/1997 | Heinrich ..................... 359/510 |
| 5,682,264 | A | * | 10/1997 | Cleveland et al. .......... 359/510 |
| 6,024,454 | A | * | 2/2000 | Horan et al. ................ 359/510 |
| 6,116,741 | A | * | 9/2000 | Paschal ...................... 359/510 |
| 2004/0156100 | A1 | * | 8/2004 | Fuchs et al. ................ 359/368 |
| 2004/0190140 | A1 | * | 9/2004 | Bala ........................... 359/510 |

* cited by examiner

*Primary Examiner*—Ricky D. Shafer
(74) *Attorney, Agent, or Firm*—Gardner Groff Santos & Greenwald, P.C.

(57) ABSTRACT

An adapter that attaches to a surgical microscope for holding the lens cover of a sterile drape at an angle relative to the scope's objective lens, so as to eliminate the reflection (glare) of illumination off the drape lens cover as light is directed through the surgical microscope to the field of view at the patient surgical site.

15 Claims, 4 Drawing Sheets

GLARE-ELIMINATION DEVICE FOR SURGICAL MICROSCOPES

CROSS-REFERENCE TO RELATED APPLICATION

This application claims the benefit of U.S. Provisional Patent Application Ser. No. 60/504,718 filed Sep. 22, 2003, which is hereby incorporated herein by reference in its entirety for all purposes.

TECHNICAL FIELD

The present invention relates generally to sterile covers or drapes for surgical microscopes that act as a sterile barrier between the microscope and a sterile operative field.

BACKGROUND OF THE INVENTION

Surgeons in operating rooms around the world perform simple and complex surgical procedures with the use of surgical microscopes. Many of these procedures require the use of ultra small micro instruments, devices, and medical supplies. In addition, surgeons conducting these procedures are operating on extremely delicate and microscopic patient anatomy. Many of these operations could not be performed without the use of magnification—or microsurgery. As surgery typically must be conducted in a "sterile field," and because the surgical microscopes are complex instruments that would be difficult to sterilize effectively for each procedure, microsurgery typically requires that the microscope be covered or "draped" with a sterile, pliable drape. This drape serves as sterile barrier between the microscope and the patient, and protects the sterile field by allowing a surgeon who is wearing sterile surgical gloves and gowns to position the microscope over the patient without contaminating himself or the patient and sterile field. The drape also protects the surgical microscope against contamination via the transfer of bacteria, viruses, and other potentially infectious microbes from a patient to the external surfaces of the microscope. The typical surgical microscope is a costly instrument with a useful life of many years and is routinely used to conduct surgery on thousands of patients, thus making protection against contamination to the patient or patient to the microscope important.

The general shape or pattern of a typical surgical microscope drape is that of a rectangular or otherwise configured flexible sheet of material with extremities designed to fit over the optics of a variety of surgical microscope designs. As the rectangular shape is held up vertically, the top short side of the rectangle is open, the long sides of the rectangle are enclosed, and the bottom short side is enclosed with a fitting for an objective lens housing and transparent non-magnifying lens cover. Prior to sterilization, the drape is systematically folded in such a manner as to allow a person dressed in sterile gloves and gown to pull the open end of the drape over the surgical microscope. The lens cover is then fitted onto the objective lens or front lens of the microscope. Generally, the objective lens points down toward the sterile field and is the component on the microscope that is closest to the patient. Because of the close proximity of the objective lens to the patient and the sterile field, it is the component most likely to act as a conductor and/or transmitter of contamination and/or infection.

The main components of a surgical microscope include the microscope body, which houses the optics; the floor stand, ceiling, or wall mount from which the optics are suspended; and the light source. As the light source is activated, illumination is directed through the objective lens to illuminate the desired subject at a distance that is determined by the focal length (e.g., f=300 mm) or working distance of the objective lens or variable lens system of the microscope body. An image of the illuminated subject is reflected back through the objective lens and is then projected to the eyes of the microscope user via an optical pathway in a system of prisms, mirrors, and lenses in the microscope body, binoculars, and eyepieces.

However, as illuminating light passes through the objective lens, it is not uncommon for some of the light to be reflected by the drape's lens cover, creating glare. This glare may result in the creation of chromatic and spherical aberrations for the user or may block the field-of-view entirely. There have been various attempts at solutions that would resolve this problem but none are completely effective.

An attempted solution pursued by some surgical microscope users is to remove the sterile lens cover that covers the objective lens from the drape. However, this attempted solution allows a non-sterile lens to be close to the sterile field or a patient's open incision. Contamination of a surgeon's instruments is likely if any instrument inadvertently touches the exposed non-sterile objective lens of the microscope. In addition, high-speed drills are often utilized in microsurgery that cause the uncontrolled displacement of bodily fluids or bone chips up towards the unprotected objective lens of the microscope. The clinical and health risks of this attempted solution are evident.

Another attempted solution has been to create a sterile microscope drape with a "dome-shaped" objective lens cover. The purpose of the dome is to reduce refracted light. However, the properties of curvature in this type of design compromise the magnifying performance of the microscope—performance for which microscope manufacturers have strived mightily to achieve and end-users have paid handsomely to acquire. In addition, certain sterilization processes through which some drapes are subjected have been known to leave condensation on the inside of a convex lens as the drape cools down after sterilization. Regardless of whether the dome is convex or concave in nature, neither design completely eliminates chromatic or spherical aberrations or undesirable glare. The result is that users of dome drapes must force their eyes to accommodate aberrations caused by the design. This can expedite and increase eyestrain and fatigue and may even cause headaches in some users. Aside from the optical shortcomings of dome covers, end users of this design continue to complain about unwanted glare or continue to compromise aseptic technique by removing the sterile dome-shaped objective lens cover.

Yet another attempted solution offered by a surgical microscope manufacturer involves removing the sterile lens cover from the drape and installing a sterile slanted lens cover. The slanted lens has proven to be very effective at completely eliminating the unwanted glare described heretofore. However, this methodology produces other undesirable issues: (1) the slanted lens must be sterilized every time it is used. This redundant process is expensive and inconvenient when personnel labor and sterilization costs are calculated, (2) the slanted lens itself is proprietary and is not inexpensive, (3) given the rigors of the operating room environment, a reasonable likelihood exists that the lens may become lost or broken, (4) there is a possibility that the person installing the sterile slanted lens prior to each procedure may become contaminated when interfacing with the non-sterile microscope body.

And finally, an attempted solution has emerged which utilizes a sterile microscope drape that includes a slanted lens cover. The housing of the slanted lens cover is inserted onto the bottom of the microscope objective lens during the microscope draping process and is held in place by friction. However, due to the lens angle necessary to eliminate unwanted glare, the drape of the objective lens housing is excessively tall and presents additional challenges for compact packaging. In addition, sterile microscope drapes currently in use worldwide typically do not utilize a tall objective lens housing but rather a low-profile housing. So the height of this tall slanted lens cover housing reduces the working distance (the distance from the surgical site to the bottom of the objective lens) available to the surgeon. As predetermined and precise working distances are important to surgeons, this proposed solution can be cumbersome and generally is not practical for many types of modern microsurgery. In addition, the requirement for a specialized drape of this sort can present availability and cost problems not present when standard drapes are used.

Accordingly, it can be seen that needs exist for improvements to surgical drapery and/or microscopes to eliminate or at least significantly reduce the glare experienced by microscope users without compromising microscope optical performance, sterility, or surgeon technique. It is to the provision of such a solution that the present invention is primarily directed.

SUMMARY OF THE INVENTION

The present invention includes an adapter device that semi-permanently attaches to a surgical microscope for the purpose of allowing any standard low profile microscope drape (flat lens or dome-shaped lens) to be utilized without the occurrence of unwanted glare. This device preferably covers the outside of the microscope's objective lens as opposed to being attached to the bottom of the lens. It can be attached to the outside of the objective lens either by set screws that grasp the outside of the objective lens casing, via the ultra fine recessed threads that already exist above the objective lens on the inside of the microscope bodies of some microscope manufacturers, by a clamp that slides over the outside ring of the objective lens and is tightened with tension inducing or clamping screws, or by an insert and twist design that also exists inside the microscope bodies of some manufacturers. The adapter device holds a standard low-profile drape objective lens cover housing in an angled or slanted orientation relative to the scopes objective lens, and thereby eliminates unwanted glare without the cumbersome tall housing associated with drape products having a built-in slanted lens cover. As a multitude of flat lens cover drape products are on the market today, availability and cost concerns are minimized. And the optical integrity of the microscope magnification, clarity, depth-of-focus, working distance and resolution are not significantly compromised by the invention, while glare is eliminated or at least reduced. Furthermore, the invention allows optimal optical performance without compromising aseptic or individual surgeon technique.

In one aspect, the invention is a device for use with a surgical microscope and a sterile drape for performing surgery on a patient, the surgical microscope having an objective lens and the drape having a cover lens. The device comprises a first part for attaching to the surgical microscope, a second part for attaching to the sterile drape, and a body between the first part and the second part, wherein the body is configured to dispose the drape cover lens in general alignment with and at an angle relative to the microscope objective lens to eliminate or reduce glare on the objective lens without significantly reducing available workspace between the cover lens and the patient.

In another aspect, the invention is a system for creating a sterile barrier for a surgical microscope for performing surgery on a patient, the microscope having an objective lens. The system comprises, a sterile drape having a cover sheet with an aperture, a peripheral frame in the aperture, and a cover lens in the frame. Additionally, the system comprises an adapter having a first part for attaching to the surgical microscope, a second part for attaching to the sterile drape, and a body between the first part and the second part, wherein the body is configured to dispose the drape cover lens in general alignment with and at an angle relative to the microscope objective lens to eliminate or reduce glare on the objective lens without significantly reducing available workspace between the cover lens and the patient.

In another aspect, the invention is a combination of a surgical microscope having an objective lens and an adapter attached to the surgical microscope adjacent to the objective lens. The adapter has an angularly offset body in which a drape mounted onto the adapter is held with a lens cover portion of the drape oriented at an acute angle relative to the objective lens of the microscope.

In still another aspect, the invention is a method of reducing or eliminating the glare in the surgical microscope, in which a sterile drape is attached to the microscope with an angularly-offset adapter that holds a lens cover portion of the drape at an acute angle relative to an objective lens portion of the microscope.

And in another aspect, the invention is an adapter for reducing glare in a surgical microscope, in which a first coupling for a removable attachment to the surgical microscope is adjacent an objective lens portion thereof. The invention also has a second coupling for removable engagement with a sterile drape having a lens cover portion. The adapter has an angularly-offset body in which the first coupling and the second coupling are oriented at an angle of between about fifteen to about twenty-two degrees relative to one another.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of exemplary embodiments of the invention, and are not restrictive of the invention as claimed.

DETAILED DESCRIPTION OF EXEMPLARY EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
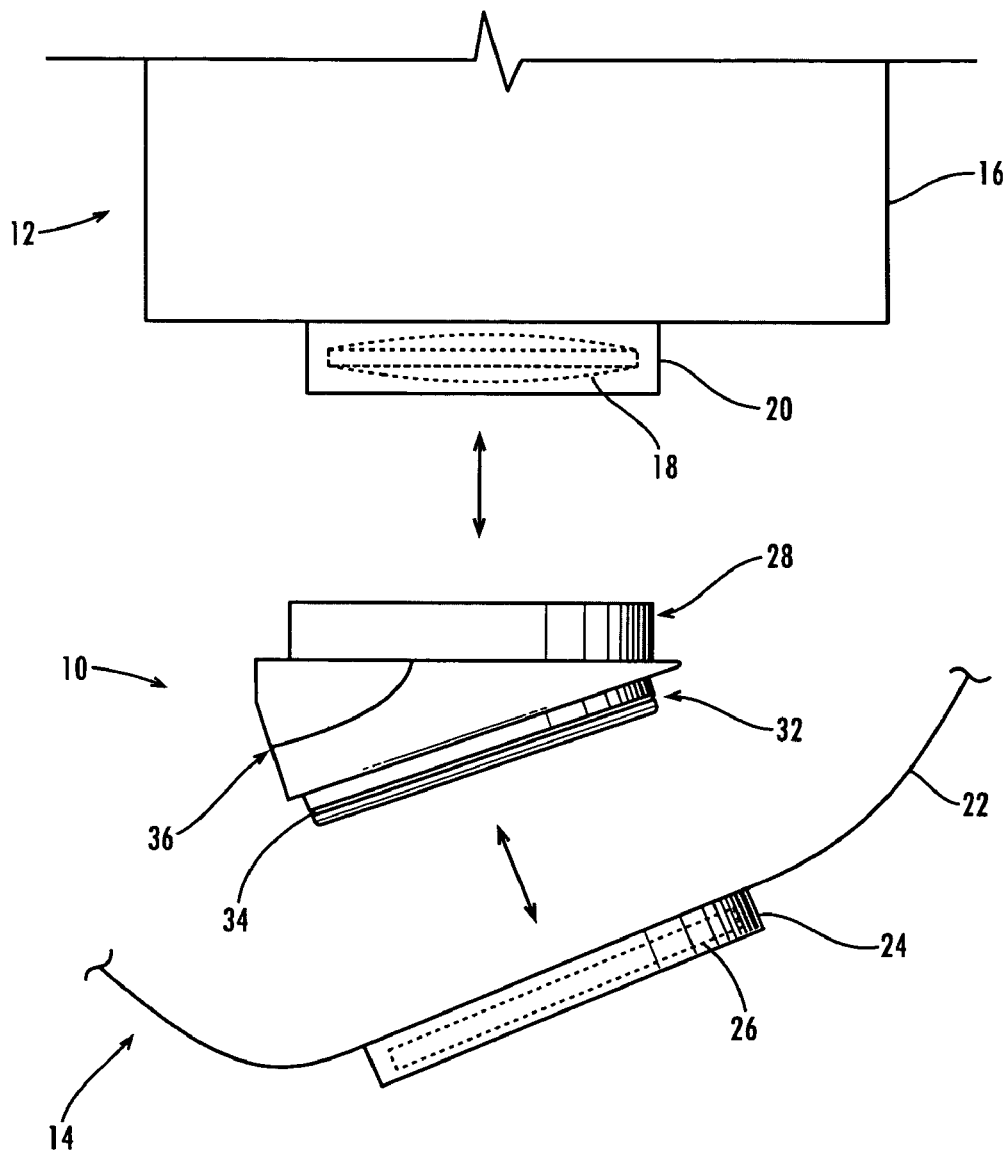
FIG. 1 is an exploded elevational view of a portion of a surgical microscope, a portion of a sterile microscope drape, and an adapter according to a first exemplary embodiment of the present invention.
Figure 2:
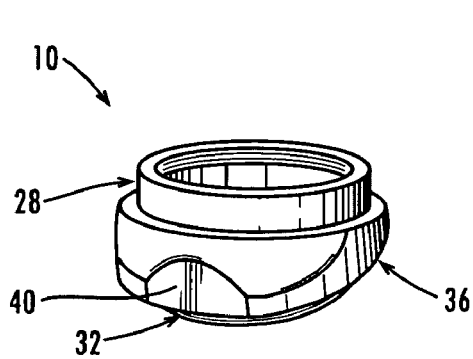
FIG. 2 is a front elevational view of the adapter of FIG. 1.

Referring now to the drawing figures, FIGS. 1–8 show an adapter device 10 according to a first exemplary embodiment of the present invention. FIG. 1 depicts the adapter 10 used in conjunction with a surgical microscope 12 and a sterile drape 14 for performing surgery on objects. Conventional surgical microscopes 12 have a body 16 with an objective lens 18 in a lens casing 20. Typical surgical microscopes 12 with which the adapter 10 may be used include the M500+ series microscopes by LEICA MICROSCOPY SYSTEMS, LTD. of Switzerland, the Opmi Sensera and Opmi Pentera microscopes by CARL ZEISS, INC., as well as many other scopes made by various manufacturers. Conventional drapes 14 have a cover sheet 22 with an aperture, a peripheral frame 24 secured in the aperture, and a non-magnifying transparent lens cover 26 mounted in the frame. Typical drapes 14 with which the adapter 10 of the present invention can be used include CLEAR IMAGE drapes by BUYMD, INC. of Atlanta, Ga. (additional information online at buymd dot net), as well as many other drapes sold by various other sources.

The adapter 10 comprises a first end 28 with a first fitting for attaching to the surgical microscope 12. For example, the fitting may be provided by an internally threaded flange 30 (FIG. 4) for mating with threads on the casing 20 of the surgical microscope 12. In alternative embodiments, the first fitting includes set screws that grasp the outside of the objective lens casing, an insert-and-twist design, a clamp design, and/or another screw-on design with threaded mating components. It will be understood that the invention is intended to include various other first fitting designs that permit semi-permanent attachment to conventional surgical microscopes so that the adapter can be removed for replacement or cleaning but is secured firmly in place on the microscope for repeated use with a number of drapes that are attached and detached without compromising the secureness of the attachment of the first fitting.

The adapter 10 further comprises a second end 32 with a second fitting for attaching to the sterile drape 14. For example, the fitting may be provided by a snap-tight fitting 34 having an external ridge and/or notch for mating with an internal ridge and/or notch in the cover lens frame 24 of the drape 14. In alternative embodiments, the second fitting includes an insert-and-twist design, a clamp design, a screw-on design, another snap-tight fitting, and/or another friction fitting. In other alternative embodiments, the adapter second fitting and the drape lens frame are keyed for use together. For example, the adapter second end may have a tab and the drape lens frame may have a notch that receives the tab (or vice versa). In this manner, the manufacturer and the practitioner can ensure that the intended drape is used with a given model of microscope, to avoid compatibility and/or performance problems, or to prevent the use of inferior grades of drapes with the adapter. It will be understood that the invention is intended to include other second fitting designs that permit quick attachment to and detachment from conventional drapes so that a drape can be easily and securely installed on the adapter for use and then easily be removed from the adapter after use, so that another drape can be installed for the next procedure.

Figure 3:
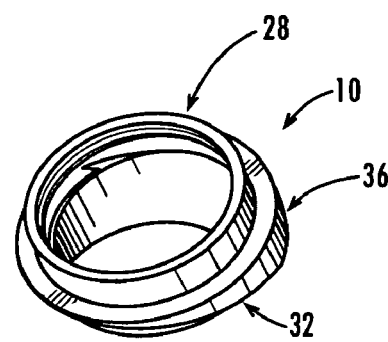
FIG. 3 is a cross sectional view of the adapter taken at line A—A of FIG. 2.

Furthermore, the adapter 10 comprises a body portion 36 between the first end 28 and the second end 32. As seen in FIG. 3, the body 36 is configured to orient the drape cover lens 26 in general alignment with and at an acute angle 38 relative to the microscope objective lens 18, to eliminate or reduce glare on the objective lens without significantly reducing available working distance between the lens cover and the subject on which surgery is being performed. Preferably, the angle 38 between second end 32 and the first end 28 is between about 15 degrees to about 22 degrees, and more preferably about 18.5 degrees. Alternatively, the adapter 10 may be provided with an angle 38 that is greater or smaller, depending on the particular microscope, drape, user, and/or surgical procedure to be performed.

Figure 4:
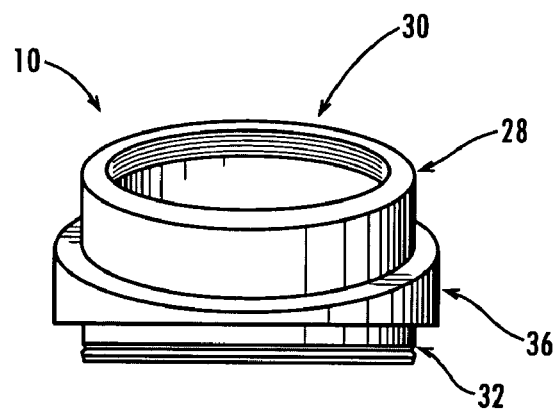
FIG. 4 is a rear perspective view of the adapter of FIG. 1.
Figure 5:
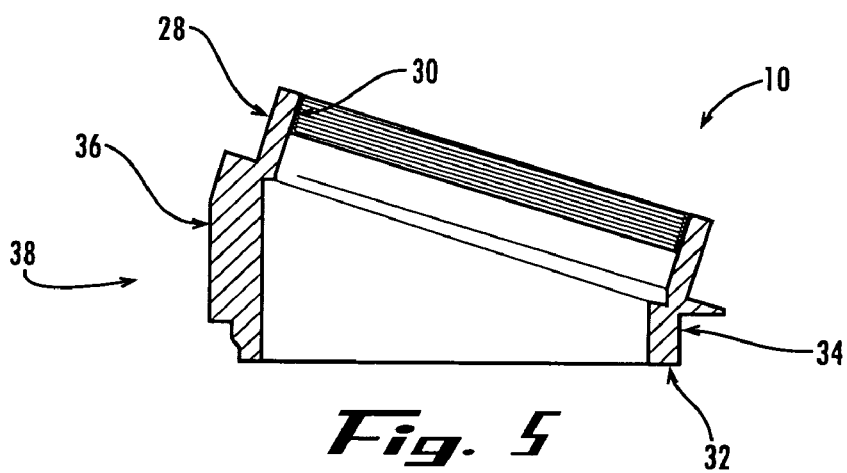
FIG. 5 is a front perspective view of the adapter of FIG. 1.
Figure 6:
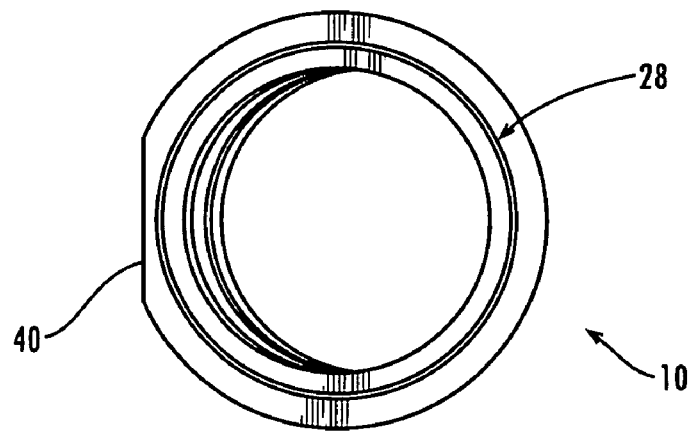
FIG. 6 is a plan view of the adapter of FIG. 1.
Figure 7:
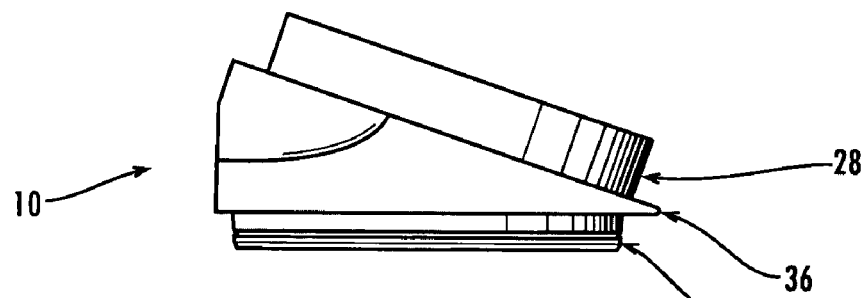
FIG. 7 is a left elevation view of the adapter of FIG. 1.
Figure 8:
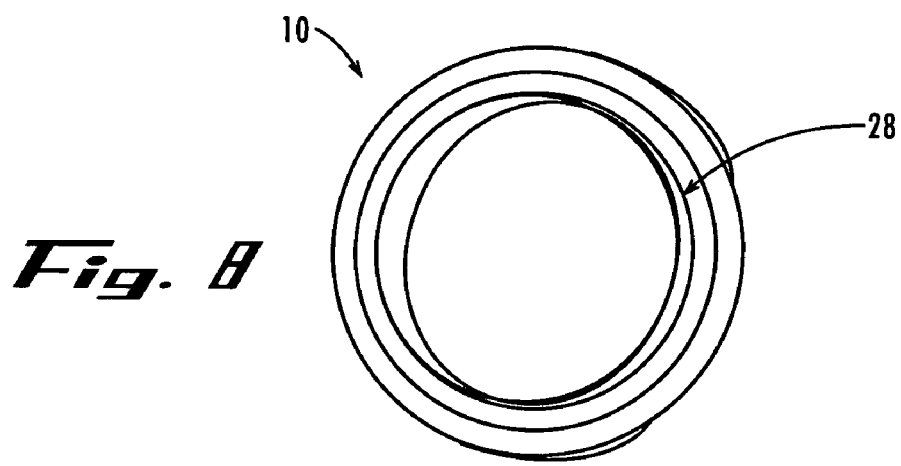
FIG. 8 is a perspective view of the adapter taken at line B—B of FIG. 7.

The adapter 10 can optionally also include a flat section or recess 40 defined in the body 36 as seen in FIG. 4. The recess 40 facilitates removing the drape 14 from the adapter 10 by providing a spot for the user to access and grasp or press against the frame 24 of the drape. Preferably, the recess 40 is generally flat or concave and positioned on the thicker side of the body 36, thereby permitting good access to the frame 24. In this way, the user can position a thumb or other finger in the recess 40 and against frame 24 to easily "pop" the frame off of the adapter.

Figure 9:
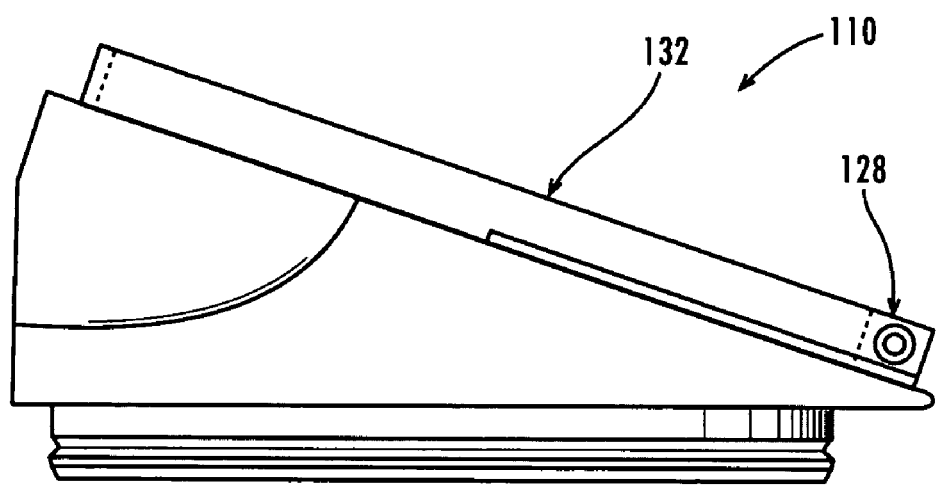
FIG. 9 is a left elevation view of an adapter according to a second exemplary embodiment of the present invention.
Figure 10:
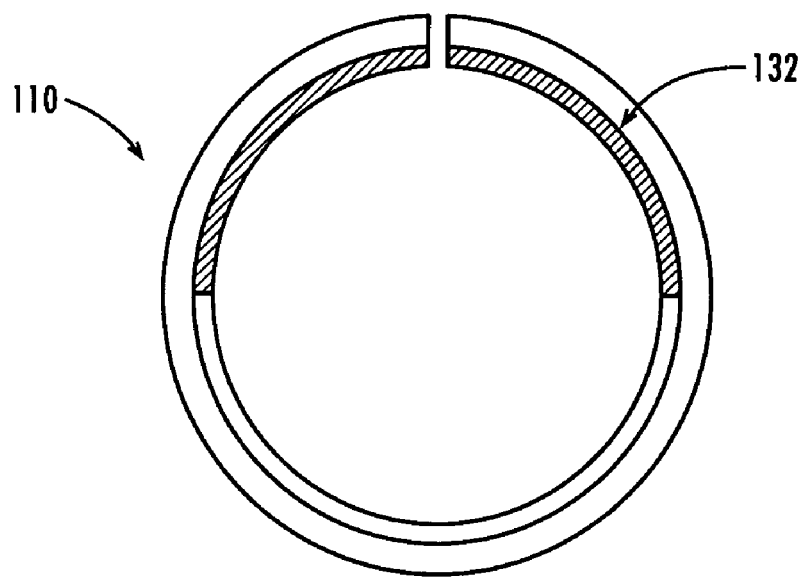
FIG. 10 is a plan view of the adapter of FIG. 9.

Referring now to FIGS. 9–10, there is shown an adapter device 110 according to a second exemplary embodiment of the present invention. In this embodiment, the first end 128 has a first fitting provided by a clamp 132 that slides over the outside casing of the objective lens of a microscope, and can then be tightened with tension-inducing or clamping screws 130, a wing-nut, thumb-screw, or other coupling. In further alternative embodiments, the invention comprises a surgical microscope having an adapter permanently or removably mounted adjacent its objective lens, the adapter having an angularly offset body, such that a drape installed on the adapter is held with its lens cover oriented at an acute angle relative to the objective lens.

In use, the adapter of the present invention is installed on the microscope by engaging the first fitting onto the microscope in a semi-permanent or permanent manner. A drape 14 is mounted onto the second fitting of the adapter. After a surgical procedure is performed, the drape is removed by detaching the drape from the second fitting, and is disposed of. A fresh drape is installed for each procedure, whereas the adapter preferably remains in place on the microscope.

Accordingly, it can be seen that the present invention provides a number of benefits over known surgical drapery and/or microscopes. In particular, the adapters of the present invention eliminate or at least significantly reduce the glare experienced by microscope users. In addition, these adapters accomplish this benefit without compromising microscope optical performance or surgeon technique.

While the invention has been described with reference to preferred and example embodiments, it will be understood by those skilled in the art that a variety of modifications, additions and deletions are within the scope of the invention, as defined by the following claims.

What is claimed is:

1. A device for use with a surgical microscope and a sterile drape for performing surgery on a patient, the surgical microscope having an objective lens and the drape having a lens cover, the device comprising:
    a first coupling for attachment to the surgical microscope;
    a second coupling for attachment to the sterile drape; and
    a body between the first coupling and the second coupling, wherein the body is configured to dispose the drape lens cover at an acute angle relative to the microscope objective lens, to eliminate or reduce glare.

2. The device of claim 1, wherein the first coupling includes a first fitting configured for semi-permanent attachment to the surgical microscope and the second coupling includes a second fitting configured for quick attachment to and detachment from the sterile drape.

3. The device of claim 2, wherein the first fitting comprises a flange with internal threads for mating with threads on the surgical microscope.

4. The device of claim 2, wherein the first fitting comprises a clamp for attaching to a casing on the surgical microscope.

5. The device of claim 1, wherein the second coupling is disposed at an angle of about 18.5 degrees relative to the first coupling.

6. A system for creating a sterile barrier for a surgical microscope for performing surgery on a patient, the microscope having an objective lens, the system comprising:
    a sterile drape having a cover sheet with an aperture, a peripheral frame in the aperture, and a lens cover in the frame; and
    an adapter having a first connector for attaching to the surgical microscope, a second connector for attaching to the sterile drape, and a body between the first connector and the second connector, wherein the body is configured to dispose the drape lens cover in general alignment with and at an acute angle relative to the microscope objective lens to eliminate or reduce glare.

7. The system of claim 6, wherein the adapter second connector and the drape lens frame are keyed for use together.

8. The system of claim 7, wherein the keying includes a tab on the adapter second end and a notch in the drape lens frame that receives the tab, or vice versa.

9. In combination, a surgical microscope having an objective lens, and an adapter attached to the surgical microscope adjacent the objective lens, said adapter comprising a first end for attachment to the surgical microscope, and a second end for releasable attachment to a drape, and an angularly offset body between the first and second ends whereby a drape mounted onto the adapter is held with a lens cover portion of the drape oriented at an acute angle relative to the objective lens of the microscope.

10. The combination of claim 9 wherein the adapter is removable from the microscope.

11. The combination of claim 10, wherein the adapter is attached to the surgical microscope by a threaded connection.

12. The combination of claim 10, wherein the adapter is attached to the surgical microscope by a clamp.

13. The combination of claim 9, wherein the adapter holds the lens cover portion of the drape at an angle of between 15–22 degrees relative to the objective lens of the microscope.

14. The combination of claim 9, further comprising the drape having a transparent lens cover portion.

15. An adapter for reducing glare in a surgical microscope, said adapter comprising a first coupling for removable attachment to the surgical microscope adjacent an objective lens portion thereof, and a second coupling for removable engagement with a sterile drape having a lens cover portion, the adapter comprising an angularly-offset body whereby the first coupling and the second coupling are oriented at an angle of between about fifteen to about twenty-two degrees relative to one another.

* * * * *